United States Patent [19]

Buysch et al.

[11] 4,335,051

[45] Jun. 15, 1982

[54] PROCESS FOR THE PREPARATION OF DIMETHYL CARBONATE

[75] Inventors: Hans-Josef Buysch; Heinrich Krimm, both of Krefeld; Siegfried Böhm, Cologne, all of Fed. Rep. of Germany

[73] Assignee: Bayer Aktiengesellschaft, Leverkusen, Fed. Rep. of Germany

[21] Appl. No.: 155,036

[22] Filed: May 30, 1980

[30] Foreign Application Priority Data

Jun. 22, 1979 [DE] Fed. Rep. of Germany ....... 2925209

[51] Int. Cl.$^3$ .............................................. C07C 68/00
[52] U.S. Cl. ................................................ 260/463
[58] Field of Search ........................................ 260/463

[56] References Cited

U.S. PATENT DOCUMENTS

2,787,631  4/1957  Stevens ................................. 260/463
3,046,255  7/1962  Strain et al. .......................... 528/371
3,326,958  6/1967  Curtius et al. ....................... 260/463

FOREIGN PATENT DOCUMENTS

2509036  9/1976  Fed. Rep. of Germany ...... 260/463

OTHER PUBLICATIONS

Derwent Abstract 60663u of French Patent 043593 (Jul. 1973).

*Primary Examiner*—Anton H. Sutto
*Attorney, Agent, or Firm*—Sprung, Horn, Kramer & Woods

[57] ABSTRACT

In a process for the preparation of dimethyl carbonate by reacting methanol with phosgene and/or methyl chloroformate, the improvement wherein the reaction is carried out in the presence of an aqueous alkali metal hydroxide solution and in the presence of an inert, water-immiscible organic solvent, at a temperature in the range from −20° C. to +40° C.

8 Claims, No Drawings

PROCESS FOR THE PREPARATION OF DIMETHYL CARBONATE

The invention relates to a process for the preparation of dimethyl carbonate by reacting methanol with phosgene and/or methyl chloroformate in the presence of an aqueous alkali metal hydroxide solution and in the presence of inert water-immiscible organic solvents.

It is known, from U.S. Pat. No. 2,787,631, to prepare dimethyl carbonate by reacting phosgene and methanol in a large excess of methyl chloroformate at the reflux temperature.

It is also known, from French Pat. No. 2,163,884, to prepare dimethyl carbonate by continuous reaction of methyl chloroformate with methanol in a column packed with Raschig rings, under reflux conditions.

Since hydrogen chloride is liberated in the abovementioned reactions of methanol with phosgene or methyl chloroformate and this compound is extremely corrosive in association with methanol, the reactions must be carried out in equipment constructed from materials which are particularly corrosion-resistant (see Kirk-Othmer, Encyclopaedia of Chemical Technology, second edition, Volume 4, page 391 (1964)), and this has an adverse effect on the profitability of the process.

A further disadvantage is that the hydrogen chloride which escapes entrains considerable amounts of starting material and end product. Troublesome and expensive separation operations, such as, for example, deep-freezing of the hydrogen chloride gas and fractional distillation of the organic products, are required to separate off these substances from the escaping hydrogen chloride.

In spite of such a troublesome purification of the hydrogen chloride gas, impurities still remain, so that the hydrogen chloride gas, because of the impurities, is unsuitable for many other purposes, for example electrolysis, and must be neutralized by washing with an alkali and removed.

In addition, the hydrogen chloride liberated initiates side reactions to a considerable extent, such as the formation of methyl chloride, dimethyl ether, water and $CO_2$ (compare, for example, J. Chem. Soc. 1935, 600 and Kirk-Othmer, Encyclopaedia of Chemical Technology, second edition, Volume 4, page 387 (1964)). Investigations also showed that such by-products are formed, in some cases in relatively large amounts, in the reaction of methanol with phosgene or methyl chloroformate.

The formation of by-products can indeed be slightly reduced by special measures, for example a low temperature, but attempts to suppress the side reactions are not successful.

Furthermore, it is necessary to burn the off-gas charged with organic material, and diluted with nitrogen for safety reasons, in order to avoid pollution of the environment. This combustion requires considerable technical effort.

Since the dimethyl carbonate prepared by reacting methanol with phosgene or methyl chloroformate contains, as described above, hydrogen chloride, methyl chloride, dimethyl ether, traces of water and unreacted methyl chloroformate and methanol as impurities, a troublesome purification operation and very effective, corrosion-resistant distillation columns are required to separate off all of these substances from the dimethyl carbonate.

A process has now been found for the preparation of dimethyl carbonate by reacting methanol with phosgene and/or methyl chloroformate, which is characterized in that the reaction is carried out in the presence of an aqueous alkali metal hydroxide solution and in the presence of an inert, water-immiscible organic solvent, at a temperature in the range from $-20°$ C. to $+40°$ C.

Useful alkali metal hydroxides, which can be used in the process according to the invention in the form of an aqueous solution, are: lithium hydroxide, sodium hydroxide, potassium hydroxide, caesium hydroxide and rubidium hydroxide; sodium hydroxide and potassium hydroxide are preferred and sodium hydroxide is particularly preferred.

The alkali metal hydroxides can be used in the process according to the invention, in the form of an aqueous solution, either individually or as mixtures with one another.

The concentration of the aqueous alkali metal hydroxide solution is not critical for the process according to the invention. However, relatively highly concentrated aqueous alkali metal hydroxide solutions are advantageously used. 15 to 50% strength by weight, preferably 25 to 48% strength by weight and particularly preferably 35 to 45% strength by weight, aqueous alkali metal hydroxide solutions are in general used.

This has the advantage that the amount of effluent can be reduced and the reaction time can be shortened.

The amount of aqueous alkali metal hydroxide solution as a rule corresponds to the amount equivalent to the amount of hydrogen chloride to be expected. About 2 to 2.6 mols, per mol of phosgene, or about 1 to 1.3 mols, per mol of methyl chloroformate, of alkali metal hydroxide are preferably employed, in aqueous solution so that the reaction proceeds rapidly and quantitatively.

Inert organic solvents which can be used in the process according to the invention are those which are not miscible with the aqueous phase and in addition can easily be separated off from dimethyl carbonate by distillation.

Inert water-immiscible organic solvents which are preferably used are: aliphatic and cycloaliphatic hydrocarbons with 1 to 30, preferably 5 to 20, carbon atoms; aromatic and araliphatic hydrocarbons with 6 to 30, preferably 6 to 10, carbon atoms; aliphatic and araliphatic ethers with 5 to 30, preferably 6 to 24, carbon atoms; and amides, nitriles and esters of aliphatic, araliphatic and aromatic carboxylic acids with 5 to 30, preferably 6 to 12, carbon atoms.

The compounds of the substance classes mentioned can optionally be monosubstituted or polysubstituted by fluorine, chlorine or bromine.

The following inert, water-immiscible organic solvents may be mentioned as examples: petroleum ether (boiling point: 50°–60° C.), pentane, isooctane, white spirit, paraffin oil, decalin, toluene, xylene, cumene, diisopropylbenzene, tetralin, dodecylbenzene, methylene chloride, 1,2-dichloropropane, n-octyl chloride, bromobenzene, chlorobenzene, dichlorobenzene, chlorotoluene, chloroxylene, diisobutyl ether, anisole, anethole, hexanenitrile, benzonitrile, benzyl cyanide, butyl dimethylacetate and butyl trimethylacetate.

Chlorobenzene, chlorotoluene, chloroxylene, bromobenzene, dichlorobenzene, xylene, cumene and diisopropylbenzene are preferred.

The amount of inert, water-immiscible organic solvents used is not critical. About 0.5 to 20 times the amount by weight relative to dimethyl carbonate is preferably used.

The solvents can be employed in the process according to the invention individually or as mixtures with one another.

The reaction temperatures of the process according to the invention are generally in the range from about −20° to about +40° C., and are preferably −10° to +35° C. and particularly preferably −5° to +30° C.

The reaction components methanol and phosgene or methyl chloroformate are generally employed in an equivalent molar ratio, but methanol can, of course, also be used in excess.

Catalysts can be added for further acceleration of the reaction, especially towards the end of the reaction.

Examples of catalysts which can be used in the process according to the invention are tertiary amines, such as triethylamine, pyridine and dimethylstearylamine, quaternary ammonium salts, such as tetrabutylammonium hydroxide and triethylbenzylammonium chloride, and quaternary phosphonium salts, such as triethylbenzylphosphonium bromide and tributylcyanoethylphosphonium chloride.

The reaction mixture obtained can be worked up, for example, by separating off the organic phase containing dimethyl carbonate from the aqueous phase, treating the organic phase with aqueous alkali metal hydroxide solution and subjecting it to fractional distillation to obtain pure dimethyl carbonate.

The first and last runnings obtained in the distillation can be recycled again immediately into the reaction.

It is exceptionally surprising that virtually no saponification of the dimethyl carbonate takes place during the treatment of the crude dimethyl carbonate with aqueous alkali metal hydroxide solution, since experiments show that severe losses in yield due to saponification of dimethyl carbonate are to be recorded in the case of treatment with solid alkalis.

Dimethyl carbonate is obtained in very good yields (up to 92%) and high purities (>99.5%) by the process according to the invention.

The process according to the invention can be carried out in various ways industrially. For example, phosgene or methyl chloroformate can be passed into a mixture of methanol, inert water-immiscible organic solvent and aqueous alkali metal hydroxide solution. Furthermore, methanol and phosgene or methyl chloroformate can be metered, separately or after prior mixing, into an aqueous alkali metal hydroxide solution. It is also possible to add the aqueous alkali metal hydroxide solution to a mixture of methanol, inert water-immiscible solvent and phosgene or methyl chloroformate.

The reaction is generally carried out at temperatures in the range from about −20° to about +40° C.

When the reaction has ended, the organic phase is separated off from the aqueous phase, then dried and treated with, for example, concentrated alkali metal hydroxide solution (for example 25 to 50% strength by weight), and, after separating off the alkali metal hydroxide solution, subjected to fractional distillation.

The first and last runnings obtained in the distillation can be recycled again immediately into the reaction mixture.

The aqueous phases are advantageously treated with inert, water-immiscible organic solvents and, after separating off the organic phase, passed to the effluent treatment plant.

The inert organic solvents can be used again for the next batch.

Dimethyl carbonate is obtained in very good yields and high purities by the process according to the invention. The process proceeds exceptionally selectively and side reactions are largely suppressed.

Since no gaseous products are liberated in the process according to the invention, working up or destruction of such products is eliminated. The process is thus particularly economic and non-polluting. Moreover, working up of the crude product, which is obtained in high purity, is most simple. Troublesome and expensive purification steps are not necessary.

Since the dimethyl carbonate obtained according to the invention contains no methyl chloroformate, working up by distillation is particularly simple. According to experiments performed by the applicant company, a very considerable technical effort is in fact required to separate off excess methyl chloroformate from dimethyl carbonate.

Moreover, it was exceptionally surprising that dimethyl carbonate could be obtained in good yields by the process according to the invention. In fact, it was to be expected that the reactive dimethyl carbonate and methyl chloroformate, which of all the chloroformates is most susceptible to hydrolysis, would undergo saponification under alkaline conditions. The good yields show, however, that virtually no saponification takes place.

Dimethyl carbonate is an important intermediate product for the preparation of polycarbonates and for the synthesis of polyurethanes.

It is also a good solvent for polymers with highly polar groups, such as polyacrylonitrile and cellulose esters (Ullmanns Enzyklopädie der technischen Chemie (Ullmann's Encyclopaedia of Industrial Chemistry), Volume 14, 4th edition, page 592).

The following examples serve to illustrate the process according to the invention, but without restricting it to these examples.

EXAMPLE 1

189 g (2 mols) of methyl chloroformate, 76 g (2.4 mols) of methanol and 800 g of chlorobenzene are cooled to 5° C., and 182.5 g of 45% strength sodium hydroxide solution (2.05 mols) are added dropwise at 5° C. in the course of 1½ hours, whilst stirring vigorously. After 10 minutes, the pH is 8 to 9. The salt is filtered off and washed with chlorobenzene. The organic layer is dried over anhydrous potassium carbonate for 45 minutes. The filtrate is subjected to fractional distillation in a 1.15 m silver-mirrored column.

First runnings of boiling point 62° to 86°: 20 g

Main runnings of boiling point 87° to 91°: 128 g; $n_{20}^D$ 1.3682

Last runnings of boiling point 92° to 130°: 10 g

The first runnings and last runnings are transferred to the next batch. The yield of dimethyl carbonate is thus increased from an initial 71% to 79 to 81% of theory. The product is 99.8% pure.

EXAMPLE 2

945 g (10 mols) of methyl chloroformate, 384 g (12 mols) of methanol and 2 kg of chlorobenzene are initially introduced into the reaction vessel. 910 g of 45% strength NaOH (10.25 mols) are added dropwise at 5° C. in the course of 5½ hours, whilst stirring. The mixture is subsequently stirred for 10 minutes. The pH value falls to 8 to 9. As much of the organic (upper) layer as possible is siphoned off and 1 liter of water is added to the residue. After the salt has largely dissolved, the upper layer is separated off. Both chlorobenzene layers are clarified through a thick flutted filter. The filtrate is distilled in a 1.15 m silver-mirrored column packed with glass rings.

| | | | |
|---|---|---|---|
| 1. | 63.5 to 70°: | 34.2 g | |
| 2. | 73 to 87°: | 46.1 g | |
| 3. | 87 to 88°: | 20.5 g; | $n_D^{20} = 1.3698$ |
| 4. | 88 to 89.5°: | 707.8 g; | $n_D^{20} = 1.3688$ (99.7% pure) |
| 5. | 90 to 94.5°: | 3.8 g; | $n_D^{20} = 1.3763$ |
| 6. | 95 to 105°: | 3.8 g; | $n_D^{20} = 1.3699$ |
| | Yield (fraction 4): | 79% of theory. | |

If fractions 1, 2, 3, 5 and 6 are added again to the next batch, the yield is increased to 85 to 88% of theory.

EXAMPLE 3

1,200 g of chlorobenzene, 284 g (3.0 mols) of methyl chloroformate and 114 g (3.6 mols) of methanol are initially introduced into a 2 l three-necked flask with a stirrer. The solution is cooled to 0° to 5° C. 275 g of 45% strength NaOH (3.09 mols) are added dropwise in the course of 6 hours, whilst stirring vigorously, and the mixture is subsequently stirred for 30 minutes. The cooling system is removed and 565 g of distilled water are added. The sodium chloride precipitated during the addition of NaOH dissolves, and two water-clear phases are obtained. The mixture is subsequently stirred for 30 minutes, without controlling the temperature, and the lower aqueous phase is separated off. The aqueous phase weighs about 980 g and the organic phase weighs 1,450 g.

The organic phase is stirred with 145 g of 45% strength NaOH for 10 minutes. The aqueous phase is separated off and used to dry the chlorobenzene for the extraction. The organic phase is subjected to fractional distillation in a silver-mirrored column. The first runnings and last runnings are included in the next experiment. The chlorobenzene remaining in the distillation flask is used as the extraction agent in the next experiment.

The aqueous phase is stirred with 1,200 g of fresh chlorobenzene for 15 minutes and passed to the effluent treatment plant. The chlorobenzene phase is used as the solvent in the next batch and, before use, is dried with the abovementioned 145 g of 45% strength NaOH. The NaOH used for the drying is used in the next batch.

Yield of crude solution: about 90% of theory.

EXAMPLE 4

910 g of 45% strength sodium hydroxide solution (10.25 mols) are added dropwise to a mixture of 945 g (10 mols) of methyl chloroformate, 87 g of the first runnings from an analogous preceding batch, 6 g of the last runnings and 348 g (12 mols) of methanol in 2 kg of o-dichlorobenzene at 5° C. in the course of 5½ hours, whilst stirring.

After a further 15 minutes, 1.2 l of water are added, the aqueous phase is separated off and extracted with about 100 g of dichlorobenzene and the organic phase is clarified by filtration over a cellulose bed and distilled in a 1.20 m mirrored packed column.

113 g of first runnings (boiling point: 63° to 89°) and a main fraction of 765 g (boiling point: 89° to 90°; $n_D^{20}=1.3688$, corresponding to 85% of theory of dimethyl carbonate (99.8% pure)) are obtained. The last runnings weigh 5 g (boiling point: 90° to 165° C.).

What is claimed is:

1. In a process for the preparation of of dimethyl carbonate by reacting methanol with phosgene and/or methyl chloroformate, the improvement wherein the reaction is carried out in the presence of a 15 to 50 percent by weight aqueous alkali metal hydroxide solution and in the presence of an inert, water-immiscible organic solvent, at a temperature in the range from −20° C. to +40° C., employing 2 to 2.6 mols, per mol of phosgene, or 1 to 1.3 mols, per mol of methylchloroformate, of said alkali metal hydroxide.

2. A process according to claim 1 wherein a sodium hydroxide solution and/or potassium hydroxide solution is used as the alkali metal hydroxide solution.

3. A process according to claim 1 wherein an aliphatic or cycloaliphatic hydrocarbon with 1 to 30 carbon atoms, an aromatic or araliphatic hydrocarbon with 6 to 30 carbon atoms, and aliphatic or araliphatic ether with 5 to 30 carbon atoms or an amide, nitrile or ester of an aliphatic, araliphatic or aromatic carboxylic acid with 5 to 30 carbon atoms, all of which compounds can optionally be substituted by fluorine, chlorine or bromine, is used as the inert water-immiscible organic solvent, individually or in admixture with one another.

4. A process according to claim 1 wherein xylene, cumene, chlorobenzene, chloroxylene, dichlorobenzene, diisopropylbenzene or bromobenzene is used as the inert water-immiscible organic solvent.

5. A process according to claim 1 wherein an organic solution containing crude dimethyl carbonate obtained in accordance with claim 1 is thereafter treated with 25 to 50 percent strength by weight aqueous alkali metal hydroxide solution, the alkali metal hydroxide solution is separated off and the organic phase is worked up by distillation.

6. A process according to claim 1 wherein methanol is reacted with phosgene.

7. A process according to claim 1 wherein methanol is reacted with methyl chloroformate.

8. A process according to claim 1, wherein said dimethyl carbonate is prepared by reacting said methanol with phosgene and/or methyl chloroformate in the presence of said water-immiscible organic solvent and said aqueous alkali metal hydroxide solution in a reaction mixture consisting essentially of said methanol, said alkali metal hydroxide solution, said inert water-immiscible organic solvents and said phosgene and/or methyl chloroformate.

* * * * *